US012606719B2

(12) United States Patent
Lee-Sepsick

(10) Patent No.: US 12,606,719 B2
(45) Date of Patent: Apr. 21, 2026

(54) METHODS AND COMPOSITIONS COMPRISING BIODEGRADABLE CYANOACRYLATES

(71) Applicant: FEMASYS, INC., Suwanee, GA (US)

(72) Inventor: Kathy Lee-Sepsick, Suwanee, GA (US)

(73) Assignee: Femasys Inc., Suwanee, GA (US)

( * ) Notice: Subject to any disclaimer, the term of this patent is extended or adjusted under 35 U.S.C. 154(b) by 849 days.

(21) Appl. No.: 16/483,428

(22) PCT Filed: Feb. 8, 2018

(86) PCT No.: PCT/US2018/017484
§ 371 (c)(1),
(2) Date: Aug. 4, 2019

(87) PCT Pub. No.: WO2018/148453
PCT Pub. Date: Aug. 16, 2018

(65) Prior Publication Data

US 2020/0010728 A1 Jan. 9, 2020

Related U.S. Application Data

(60) Provisional application No. 62/456,916, filed on Feb. 9, 2017.

(51) Int. Cl.

| | |
|---|---|
| ***C09J 4/00*** | (2006.01) |
| ***A61L 24/00*** | (2006.01) |
| ***A61L 24/06*** | (2006.01) |
| ***C08F 222/32*** | (2006.01) |

(52) U.S. Cl.
CPC ............. *C09J 4/00* (2013.01); *A61L 24/0042* (2013.01); *A61L 24/06* (2013.01); *C08F 222/327* (2020.02); *A61L 2430/36* (2013.01)

(58) Field of Classification Search
CPC .. A61L 24/0042; A61L 24/06; A61L 2430/36; C08F 222/327; C09J 4/00
See application file for complete search history.

(56) References Cited

U.S. PATENT DOCUMENTS

| | | | |
|---|---|---|---|
| 2,721,858 A | 10/1955 | Joyner et al. | |
| 2,784,127 A | 3/1957 | Joyner et al. | |
| 3,254,111 A | 5/1966 | Hawkins et al. | |
| 3,527,224 A | 9/1970 | Rabinowitz | |
| 3,564,078 A | 2/1971 | Wicker et al. | |
| 3,591,676 A | 7/1971 | Hawkins et al. | |
| 3,667,472 A | 6/1972 | Halpern | |
| 3,704,089 A | 11/1972 | Stehlik | |
| 3,940,362 A | 2/1976 | Overhults | |
| 3,995,641 A | 12/1976 | Kronenthal et al. | |
| 4,035,334 A | 7/1977 | Davydov et al. | |
| 4,364,876 A | 12/1982 | Kimura et al. | |
| 4,444,933 A | 4/1984 | Columbus et al. | |
| 4,650,826 A | 3/1987 | Waniczek et al. | |
| 6,143,805 A | 11/2000 | Hickey et al. | |
| 6,579,469 B1 * | 6/2003 | Nicholson | A61L 24/001 524/297 |
| 8,048,086 B2 | 11/2011 | Lee-Sepsick et al. | |
| 8,048,101 B2 | 11/2011 | Lee-Sepsick et al. | |
| 8,052,669 B2 | 11/2011 | Lee-Sepsick et al. | |
| 8,316,853 B2 | 11/2012 | Lee-Sepsick et al. | |
| 8,316,854 B2 | 11/2012 | Lee-Sepsick et al. | |
| 8,324,193 B2 | 12/2012 | Lee-Sepsick et al. | |
| 8,336,552 B2 | 12/2012 | Lee-Sepsick et al. | |
| 8,695,606 B2 | 4/2014 | Lee-Sepsick et al. | |
| 8,726,906 B2 | 5/2014 | Lee-Sepsick et al. | |
| 9,034,053 B2 | 5/2015 | Lee-Sepsick et al. | |
| 9,220,880 B2 | 12/2015 | Lee-Sepsick et al. | |
| 9,554,826 B2 | 1/2017 | Lee-Sepsick et al. | |
| 2007/0024846 A1 | 2/2007 | Allweier | |
| 2007/0248486 A1 * | 10/2007 | Morales | A61L 2/087 424/78.27 |
| 2009/0024108 A1 * | 1/2009 | Lee-Sepsick | A61P 15/00 424/9.1 |
| 2012/0003153 A1 | 1/2012 | Peters et al. | |
| 2012/0004288 A1 | 1/2012 | Worm | |
| 2012/0042880 A1 | 2/2012 | Lee-sepsick et al. | |
| 2012/0315340 A1 | 12/2012 | Crudden et al. | |
| 2014/0163610 A1 * | 6/2014 | Zhang | A61L 26/0066 606/214 |

(Continued)

FOREIGN PATENT DOCUMENTS

| | | |
|---|---|---|
| BR | 112019015714 | 3/2020 |
| CA | 3050319 | 8/2018 |
| CN | 103083718 | 5/2013 |

(Continued)

OTHER PUBLICATIONS

Machado et al. 'Study of dentinal adhesives compatibility using histological analysis', Braz J Oral Sci., 2007, vol. 6, No. 20, pp. 1289-1294.
PCT Search Report, Issued May 7, 2018, in PCT/US18/17484, inventor K. Lee-Sepsick (3 pgs).
PCT Written Opinion, Issued May 7, 2018, in PCT/US18/17484, inventor K. Lee-Sepsick (5 pgs).
PCT Search Strategy, Issued May 7, 2018, in PCT/US18/17484, inventor K. Lee-Sepsick (3 pgs).
Office Action, issued Oct. 11, 2022, in Brazilian Patent Application No. BR112019015714-0, filed Aug. 2, 2018; Applicant, Femasys Inc., 4 p.
Office Action, issued Apr. 19, 2022, in Brazilian Patent Application No. BR112019015714-0, filed Aug. 2, 2018; Applicant, Femasys Inc., 7 p.

(Continued)

*Primary Examiner* — James C Goloboy
(74) *Attorney, Agent, or Firm* — Schwegman Lundberg & Woessner, P.A.

(57) ABSTRACT

Disclosed herein are methods of making and using cyanoacrylate compositions comprising one or more cyanoacrylates, a high level of at least one stabilizing agent and at least one free-radical polymerization inhibitor. Methods disclosed comprise making such compositions and using such compositions, for example, for occluding conduits such as fallopian tubes.

7 Claims, No Drawings

(56) References Cited

U.S. PATENT DOCUMENTS

| | | | |
|---|---|---|---|
| 2014/0369952 A1 | 12/2014 | Liu et al. | |
| 2019/0175782 A1 | 6/2019 | Shen | |

FOREIGN PATENT DOCUMENTS

| | | |
|---|---|---|
| CN | 105079856 | 11/2015 |
| CN | 110267687 | 9/2019 |
| EP | 0659441 | 3/2002 |
| EP | 3579890 | 6/2025 |
| HK | 40007722 | 6/2020 |
| HK | 40018048 | 9/2020 |
| IN | 430804 | 5/2023 |
| JP | H07252455 | 10/1995 |
| JP | 2002503522 | 2/2002 |
| JP | 2009120851 | 6/2009 |
| JP | 4916102 | 2/2012 |
| JP | 201209880 | 4/2012 |
| JP | 2002322220 | 11/2012 |
| JP | 2020508367 | 3/2020 |
| JP | 7252455 | 3/2023 |
| JP | 7379157 | 11/2023 |
| JP | 2024023211 | 2/2024 |
| JP | 7594647 | 11/2024 |
| KR | 100523662 | 10/2005 |
| KR | 20190112135 | 10/2019 |
| KR | 102713236 | 9/2024 |
| WO | 99/42142 | 8/1999 |
| WO | 2001089501 | 11/2001 |
| WO | 2004106284 | 12/2004 |
| WO | 2018148453 | 8/2018 |

OTHER PUBLICATIONS

Office Action, issued May 31, 2022, in Chinese Patent Application No. 2018800109689, filed Aug. 2, 2018, Applicant, Femasys Inc., 11 p.
Office Action, issued May 24, 2021, in Chinese Patent Application No. 2018800109689, filed Aug. 2, 2018, Applicant, Femasys Inc., 8 p.
Extended European Search Report, issued Dec. 8, 2020, in European Patent Application No. 18751753.7, filed Aug. 2, 2018, Applicant, Femasys Inc., 8 p.
First Examination Report, issued Jan. 31, 2022 , in Indian Patent Application No. 201917028409, filed Aug. 2, 2018, Applicant, Femasys Inc., 6 p.
Office Action, issued Feb. 14, 2022, in Japanese Patent Application No. 2019-542727, filed Aug. 2, 2018, Applicant, Femasys Inc., 2 p.
Office Action, issued Sep. 19, 2022, in Korean Patent Application No. 10-2019-7026332, filed Aug. 2, 2018, Applicant, Femasys Inc., 8 p.
Notice of Allowance in decision published in the Official Gazette n° 2722, Mar. 7, 2023, and translation, for Brazilian Patent Application No. BR112019015714-0, filed Feb. 8, 2018; Applicant, Femasys Inc., 2 p.
Office Action, issued Apr. 19, 2024, in Canadian patent application No. 3050319, filed Feb. 8, 2018; Applicant, Femasys Inc., 5 p.
Interview, issued Jun. 25, 2025, in Canadian patent application No. 3050319, filed Feb. 8, 2018; Applicant, Femasys Inc., 1 p.
Rejection Decision and translation, issued Feb. 24, 2023, in Chinese Patent Application No. 2018800109689, filed Aug. 2, 2018, Applicant, Femasys Inc., 24 p.
Office Action, issued May 3, 2023, in European Patent Application No. 18751753.7, filed Feb. 8, 2018, Applicant, Femasys Inc., 4 p.
Decision to Grant, issued May 25, 2025, in European Patent Application No. 18751753.7, filed Feb. 8, 2018, Applicant, Femasys Inc., 2 p.
Transmission of granted Patent, issued Jul. 1, 2025, in European Patent Application No. 18751753.7, filed Feb. 8, 2018, Applicant, Femasys Inc., 41p.
Patent Grant, issued May 1, 2023, in Indian Patent Application No. 201917028409, filed Aug. 2, 2018, Applicant, Femasys Inc., 1 p.
Second Office Action, translation, issued Oct. 4, 2022, in Japanese Patent Application No. 2019-542727, filed Aug. 2, 2018, Applicant, Femasys Inc., 3 p.
Third Office Action, translation, issued May 16, 2023, in Japanese Patent Application No. 2019-542727, filed Aug. 2, 2018, Applicant, Femasys Inc., 6 p.
Decision to Grant, translation, issued Oct. 3, 2023, in Japanese Patent Application No. 2019-542727, filed Aug. 2, 2018, Applicant, Femasys Inc., 5 p.
Certificate of Patent, issued Nov. 6, 2023, in Japanese Patent Application No. 2019-542727, filed Aug. 2, 2018, Applicant, Femasys Inc., 2 p.
Decision to Grant, translation, issued in Japanese Patent Application No. 2023-187621, filed Nov. 1, 2023, Applicant, Femasys Inc., 2 p.
Filing Receipt, translation, issued Nov. 1, 2023, in Japanese Patent Application No. 2023-187621, filed Nov. 1, 2023, Applicant, Femasys Inc., 2 p.
Decision to Grant, translation, issued Nov. 12, 2023, in Japanese Patent Application No. 2023-187621, filed Nov. 1, 2023, Applicant, Femasys Inc., 6 p.
Patent Certificate, issued Nov. 26, 2024, in Japanese Patent Application No. 2023-187621, filed Nov. 1, 2023, Applicant, Femasys Inc., 2 p.
Final Rejection, translation, issued May 30, 2023, in Korean Patent Application No. 10-2019-7026332, filed Feb. 8, 2018, Applicant, Femasys Inc., 10 p.
NonFinal Rejection, translation, issued Sep. 26, 2023, in Korean Patent Application No. 10-2019-7026332, filed Feb. 8, 2018, Applicant Femasys Inc., 10 p.
Notice of Allowance, issued Jun. 27, 2024, in Korean Patent Application No. 10-2019-7026332, Filed Feb. 8, 2018, Applicant Femasys Inc., 8 p.
"European Application Serial No. 25182956.0, Extended European Search Report mailed Nov. 17, 2025", 7 pgs.
"Canadian Application Serial No. 3,050,319, Response filed Aug. 9, 2024 to Office Action mailed Apr. 19, 2024", 10 pgs.
"European Application Serial No. 18751753.7, Response filed Jul. 20, 2021 to Extended European Search Report mailed Dec. 8, 2020", 11 pgs.
"European Application Serial No. 18751753.7, Response filed Jun. 15, 2023 to Communication Pursuant to Article 943 EPC mailed May 3, 2023", 97 pgs.
"Korean Application Serial No. 10-2019-7026332, Response filed Dec. 21, 2022 to Notice of Preliminary Rejection mailed Sep. 19, 2022", W English Claims, 37 pgs.
"Korean Application Serial No. 10-2019-7026332, Response filed Aug. 11, 2023 to Final Rejection mailed May 30, 2023", W English Claims, 27 pgs.
"Korean Application Serial No. 10-2019-7026332, Response filed Dec. 15, 2023 to Non Final Rejection mailed Sep. 26, 2023", W English Claims, 17 pgs.
"Japanese Application Serial No. 2019-542727, Notification of Reasons for Rejection mailed Jan. 11, 2022", W English Translation, 6 pgs.
"Japanese Application Serial No. 2019-542727, Response filed Jun. 27, 2022 to Notification of Reasons for Rejection mailed Jan. 11, 2022", 2 pgs.
"Japanese Application Serial No. 2019-542727, Response filed Mar. 16, 2023 to Notification of Reasons for Rejection mailed Oct. 4, 2022", 3 pgs.
"Japanese Application Serial No. 2019-542727, Response filed Jul. 13, 2023 to Notification of Reasons for Rejection mailed May 16, 2023", 6 pgs.
"Indian Application Serial No. 202244057646, Response filed Jul. 27, 2022 to First Examination Report mailed Jan. 31, 2022", 8 pgs.

* cited by examiner

METHODS AND COMPOSITIONS COMPRISING BIODEGRADABLE CYANOACRYLATES

RELATED APPLICATIONS

This application is a nonprovisional patent application filed under 35 U.S.C. § 371, which claims the priority of and benefit of filing of PCT/US18/17484, filed Feb. 8, 2018, which claims the priority of and the benefit of the filing date of U.S. Provisional Patent Application Ser. No. 62/456,916, filed Feb. 9, 2017, each of which is herein incorporated in its entirety.

TECHNICAL FIELD

The present disclosure relates to methods and compositions comprising cyanoacrylates for medical and veterinary uses.

BACKGROUND

In the medical and research fields, cyanoacrylates have been used as tissue adhesives. Cyanoacrylates that are known in the art are generally formulated for an intended use, and may comprise additives. Cyanoacrylates can be represented by the following formula:

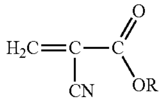

wherein R is an alkyl group or other suitable substituent forming the ester component of the molecule. Such cyanoacrylates are disclosed in U.S. Pat. Nos. 3,527,224; 3,591,676; 3,667,472; 3,995,641; 4,035,334; and 4,650,826, and making such compounds is known in the art. Typically, when used with living tissue, the R substituent is most often lower alkyl (i.e. $C_1$ to $C_8$) and the corresponding alkyl cyanoacrylate esters are liquid at room temperature. It is well known that lower alkyl cyanoacrylate esters tend to form a brittle polymer that lacks long term integrity due to cracking.

Common cyanoacrylate compositions include those for use as an adjunct to surgical sutures and staples in wound closure as well as for covering and protecting surface wounds, such as lacerations, abrasions, burns, stomatitis, sores and other surface wounds. These topical medical applications require the cyanoacrylate to form a polymer layer to inhibit blister formation and provide a protective barrier of film for the skin while minimizing a histological response. The most commonly used topical cyanoacrylates compositions consist of octyl, butyl or a blend that incorporates low levels of sulfur dioxide so as to not inhibit the rate of polymerization while minimizing an histological response. Other components such as plasticizers are added to the compositions to increase flexibility despite the challenges of compatibility of components and the weakening of the adhesive qualities of the composition.

What is needed are compositions that initiate tissue reactions and cause occlusions to form in conduits.

SUMMARY

The present disclosure comprises compositions comprising at least cyanoacrylates for medical and veterinary uses, such as for the occlusion of conduits. In particular, the present disclosure comprises cyanoacrylate compositions for the occlusion of conduits in humans or other animals. The conduit may be a conduit such as a tube or vessel in the body. In certain uses, a disclosed cyanoacrylate composition comprises one cyanoacrylate or two or more cyanoacrylates that are polymerized in a at least a portion of a conduit, degrade over time while in the body, and thus tissue ingrowth or scarring maintains the occlusion once the polymerized material has degraded.

To achieve occlusion of conduits, compositions disclosed herein may comprise a blend or admixture of cyanoacrylate isomers. In an aspect, a composition may further comprise a stabilizer in a large amount, such as sulfur dioxide, and a biodegradable composition disclosed herein creates a a desired reaction of causing a tissue response that leads to a lasting occlusion.

DETAILED DESCRIPTION

Disclosed herein are methods and biodegradable composition comprising cyanoacrylates for use in medical and veterinary methods, such as occluding conduits in a subject, such as a human or animal.

Disclosed herein are biodegradable cyanoacrylate compositions comprising three components; 1) a cyanoacrylate component; 2) a stabilizer component and 3) a polymerization inhibitor component. In an aspect, a composition may comprise, a) at least about 80 wt % (weight percent) or higher of the cyanoacrylate component; b) from about 500 ppm to about 1,500 ppm of the stabilizer component; and c) from about 4,000 ppm to about 7,000 ppm of the polymerization inhibitor component, wherein the cyanoacrylate component may comprise one or more cyanoacryalates. Such biodegradable cyanoacrylate compositions may be sterile compositions. It is understood that the compositions disclosed herein are formulated as liquid compositions and that after the liquid composition is provided to a target site, the liquid composition undergoes polymerization and forms a solid material that is the result of the reactions of the components in the liquid formulation. Further, as the disclosed compositions are biodegradable (also known as absorbable or resorbable compositions), the solid material is transformed over time into its breakdown products. It will be clear to those of skill in the art in the disclosure herein where the liquid formulation is intended, where the polymerized material is intended and where the break down products are intended.

Disclosed herein are biodegradable cyanoacrylate compositions consisting essentially of three components; 1) a cyanoacrylate component; 2) a stabilizer component and 3) a polymerization inhibitor component. In an aspect, a composition may consist essentially of, a) about 90 weight percent or higher of the cyanoacrylate component; b) from about 500 ppm to about 1,500 ppm of the stabilizer component; and c) from about 4,000 ppm to about 7,000 ppm of the polymerization inhibitor component, wherein the cyanoacrylate component may comprise one or more cyanoacryalates. Such biodegradable cyanoacrylate compositions may be sterile compositions.

In an aspect, a biodegradable cyanoacrylate composition can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm of the stabilizer component; and c) about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm of the polymerization inhibitor component.

In an aspect, a biodegradable cyanoacrylate composition can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm of the stabilizer component; and c) about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm of the polymerization inhibitor component.

In an aspect, biodegradable cyanoacrylate cyanoacrylate compositions can comprise: a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5 wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, or in a range from 80 to 99.5 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm of the stabilizer component; and c) about 4,500 ppm to about 7,000 ppm; about 5,000 ppm to about 7,000 ppm; or about 6,500 ppm to about 7,000 ppm of the polymerization inhibitor component.

In an aspect, biodegradable cyanoacrylate compositions can comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm of the stabilizer component; and c) about 4,500 ppm to about 7,000 ppm; about 5,000 ppm to about 7,000 ppm; or about 6,500 ppm to about 7,000 ppm of polymerization inhibitor component.

In an aspect, biodegradable cyanoacrylate compositions can comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5% wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, 99.9 wt % or in a range from 80 to 99.9 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component; b) about 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1,075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm of the stabilizer component; and c) about 4,000 ppm, 4,250 ppm, 4,500 ppm, 4,750 ppm, 5,000 ppm, 5,250 ppm, 5,500 ppm, 5,750 ppm, 6,000 ppm, 6,250 ppm, 6,500 ppm, 6,750 ppm, or 7,000 ppm of polymerization inhibitor component.

A disclosed biodegradable cyanoacrylate composition may be referred to herein interchangeably as a cyanoacrylate composition or an occlusive composition.

A disclosed biodegradable cyanoacrylate composition may comprise at least these disclosed components, a cyanoacrylate component, a polymerization inhibitor, and a stabilizer, in combinations that affect the desired characteristics of a cyanoacrylate composition itself, the delivery of the composition, or the material formed after curing (polymerization) of the composition. Differing cyanoacrylate monomers or differing amounts of each may be included in a biodegradable cyanoacrylate composition for the following purposes, among others: to modulate charge morphology; alter physical properties of the cyanoacrylate composition, including, but not limited to, molecular weight or viscosity; alter the interaction of the cyanoacrylate composition with certain additives and other materials, such as polymers, plastics and metals; alter tissue reaction or response to the applied composition; adjust adhesion properties of the composition, including, but not limited to, polymerization rate or heat of polymerization; adjust the degradation profile of the resultant composition, including percent degradation, degradation rate, and formaldehyde production during degradation; alter physical properties of the applied cured composition, including, but not limited to, bond strength, pliability, granularity, and cohesivity.

In an aspect a biodegradable cyanoacrylate component comprises one or more types of cyanoacrylate monomers, for example monomeric esters of 2-cyanoacrylic acid of the general formula:

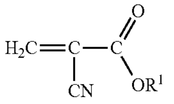

wherein $R^1$ is a hydrocarbyl or substituted hydrocarbyl group; a group having the formula:

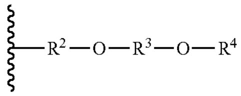

wherein $R^2$ is a 1,2-alkylene group having 2-4 carbon atoms, $R^3$ is an alkylene group having 2-12 carbon atoms, and $R^4$ is an alkyl group having 1-6 carbon atoms; or a group having the formula:

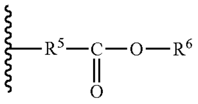

wherein $R^5$ has a formula:

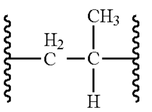

or $—[C(CH_3)_2]n-$, wherein n is an integer with a value of 1, 2, 3, 4, 5, 6, 7, 8, 9, 10, 11, 12, 13, or 14 and $R^6$ is an organic moiety.

In various aspects, the hydrocarbyl and substituted hydrocarbyl groups can be a straight chain or branched chain alkyl group having 1-16 carbon atoms; a straight chain or branched chain $C_1$-$C_6$ alkyl group substituted with an acyloxy group, a haloalkyl group, an alkoxy group, an alkyloxy group, a halogen atom, a cyano group, or a haloalkyl group; a straight chain or branched chain alkenyl group having 2 to 16 carbon atoms; a straight chain or branched chain alkynyl group having 2 to 12 carbon atoms cycloalkyl groups; an arylalkyl group; an alkylaryl group; and an aryl group. In a further aspect, the hydrocarbyl and substituted hydrocarbyl groups can be an alkyl group having 1 to 10 carbon atoms optionally substituted with a $C_1$-$C_6$ alkoxy group; an alkenyl group having 2 to 10 carbon atoms optionally substituted with a $C_1$-$C_6$ alkoxy group; a cyclohexyl group optionally substituted with a $C_1$-$C_6$ alkoxy group; or a phenyl group optionally substituted with a $C_1$-$C_6$ alkoxy group.

In an aspect, $R^1$ is selected from methyl, ethyl, n-propyl, isopropyl, n-butyl, isobutyl, pentyl, neo-pentyl, hexyl, n-octyl, 2-octyl, methoxymethyl, methoxyethyl, methoxypropyl, methoxyisopropyl, methoxybutyl, methoxyisobutyl, allyl, methallyl, crotyl, propargyl, cyclohexyl, benzyl, phenyl, cresyl, 2-chlorobutyl, trifluorethyl, 2-methoxy ethyl, 3-methoxybutyl, 2-ethoxy ethyl, and 2-propoxyethyl.

The organic moiety $R^6$ can be substituted or unsubstituted and can be a straight chain, branched or cyclic, saturated, unsaturated or aromatic. In a further aspect, such organic moieties include $C_1$-$C_8$ alkyl moieties, $C_2$-$C_8$ alkenyl moieties, $C_2$-$C_8$ alkynyl moieties, $C_3$-$C_{12}$ cycloaliphatic moieties, aryl moieties such as phenyl and substituted phenyl, and arylalkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. In a still further aspect, $R^6$ can be an alkyl, alkenyl or alkynyl moieties having from 1 to about 8 carbon atoms, and halo-substituted derivatives thereof. In a yet further aspect, $R^6$ can be an alkyl moiety of 4 to 8 carbon atoms.

In various aspects, $R^1$ is an alkyl group having 1-10 carbon atoms or a group having the formula -$AOR^7$, wherein A is a divalent straight or branched chain alkylene or oxyalkylene moiety having 2-8 carbon atoms, and $R^7$ is a straight or branched alkyl moiety having 1-8 carbon atoms. In a further aspect, a cyanoacrylate component is 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, methyl cyanoacrylate, ethyl cyanoacrylate, propyl cyanoacrylate, butyl cyanoacrylate, pentyl cyanoacrylate, hexyl cyanoacrylate, septyl cyanoacrylate, octyl nonyl cyanoacrylate, decyl 2-cyanoacrylate, allyl cyanoacrylate, methoxyethyl cyanoacrylate, methoxyisopropyl cyanoacrylate, methoxypropyl cyanoacrylate, methoxybutyl cyanoacrylate, or methoxypentyl cyanoacrylate, or a combination thereof. A cyanoacrylate component may comprise two or more methoxy cyanoacrylate monomers.

Cyanoacrylate monomers disclosed herein can be prepared by methods known in the art. For example, see U.S. Pat. Nos. 2,721,858, 3,254,111, 3,995,641 and 4,364,876, each of which is hereby incorporated in its entirety by reference, for example, for cyanoacrylate synthesis. Cyanoacrylate monomers for use in the present disclosure include aliphatic 2-cyanoacrylate esters, including, but not limited to, an alkyl, cycloalkyl, halogenated, alkenyl or alkoxyalkyl 2-cyanoacrylate. The alkyl group may have from 1-16 carbon atoms, 2-8 carbon atoms, or 1-4 carbon atoms. Suitable esters include the methyl, ethyl, n-propyl, isopropyl, isobutyl, n-butyl, sec-butyl, n-pentyl, isopentyl, n-hexyl, isohexyl, 2-ethylhexyl, cyclohexyl, n-heptyl, n-octyl, 2-octyl, 2-methoxyethyl, methoxypropyl, 2-ethoxyethyl, and 2-methoxyisopropyl esters of cyanoacrylic acid and the like. For use in medical or in vivo applications, monomers utilized are of high purity.

For example, a cyanoacrylate component may comprise a) about 80.0 wt %, 80.5 wt %, 81 wt %, 81.5 wt %, 82 wt %; 82.5 wt %; 83 wt %; 83.5 wt %; 84 wt %; 84.5 wt %, 86 wt %; 86.5 wt %; 87 wt %; 87.5 wt %, 88 wt %; 88.5 wt %, 89 wt %, 89.5 wt %, 90 wt %, 90.5 wt %, 91 wt %, 91.5 wt %, 92 wt %; 92.5 wt %; 93 wt %; 93.5 wt %; 94 wt %; 94.5 wt %, 96 wt %; 96.5 wt %; 97 wt %; 97.5 wt %, 98 wt %; 98.5 wt %, 99 wt %, 99.5 wt %, or in a range from 80 to 99.5 wt %, 80 to 95 wt %, 80 to 81 wt %, 80 to 82 wt %, 80 to 85 wt %, 84 to 86 wt %, 85 to 87 wt %, 86 to 88 wt %, 87 to 89 wt %, 88 to 90 wt %, 90 to 92 wt %, 91 to 93 wt %, 90.5 to 92.5 wt %, 91 to 93 wt %, 92 to 94 wt %, 93 to 95 wt %, 95.5 to 97.5 wt %, 94 to 96 wt %, 95 to 98 wt %, 96 to 99 wt %, 90 to 97 wt %, 90 to 95 wt % and 90 to 99.9 wt % of the cyanoacrylate component, may comprise up to about 100 wt % of the composition and all ranges therebetween 80 wt % and 100 wt %.

In an aspect, a cyanoacrylate component comprises a blend or admixture of two or more cyanoacrylate monomers in the wt % and/or ranges disclosed herein. For example, if one cyanoacrylate monomer is methyl cyanoacrylate and a second cyanoacrylate monomer is ethyl cyanoacrylate, a blend or admixture of the methyl cyanoacrylate monomer and the ethyl cyanoacrylate monomer could form a cyanoacrylate component such as those disclosed herein. In an aspect, a cyanoacrylate component comprises a single cyanoacrylate monomer in the wt % and/or ranges disclosed herein. For example, if one cyanoacrylate monomer is methyl cyanoacrylate, the methyl cyanoacrylate monomer forms a cyanoacrylate component such as those disclosed herein.

In an aspect, a stabilizer component of a cyanoacrylate composition is an anionic stabilizer. Examples of stabilizer components include, but are not limited to, the following: alkyl sulfides, alkyl sulfates, alkyl sulfonyls, alkyl sulfones, alkyl sulfoxides, alkyl sulfites, sultones (e.g., a-chloro-a-hydroxy-o-toluenesulfonic acid-y-sultone), sulfur dioxide, sulfur trioxide, sulfonic acid, lactone, boron trifluoride, organic acids, such as acetic acid, 3-sulfolene, mercaptan, and the like, and mixtures thereof. In certain applications, the stabilizer component is one or more of sulfur dioxide, sulfur trioxide, or sulfonic acid, or combinations thereof.

In an aspect, a cyanoacrylate composition can comprise an acidic stabilizing agent such as hydrogen sulfide, carbonic acid, triacetylmethane, acetic acid, lactic acid, benzoic acid, dinitrophenol, formic acid, nitrous acid, hydrochloric acid, hydrobromic acid, hydrofluoric acid, chloroacetic acid, phosphoric acid (including ortho, meta, or para-phosphoric acid), dichloroacetic acid, trichloroacetic acid, trinitrophenol (picric acid), trifluoroacetic acid, sulfuric acid, perchloric acid, toluenesulfonic acid, fluorosulfonic acid, and the like, and mixtures thereof, can be included in the cyanoacrylate composition.

A biodegradable cyanoacrylate composition may have one or more types of stabilizing agents, such as an anionic stabilizer and an acidic stabilizer.

A stabilizer component can be present at a concentration of about 500 to about 1,500 parts per million stabilizer component. In an aspect, a stabilizer component is present in an amount of about 500 ppm to about 550 ppm; 500 ppm to about 600 ppm; about 500 ppm to about 650 ppm; about 500 ppm to about 700 ppm; about 500 ppm to about 750 ppm; about 500 ppm to about 800 ppm; about 500 ppm to about 850 ppm; about 500 ppm to about 900 ppm; about 500 ppm to about 950 ppm; about 500 ppm to about 1000 ppm; about 500 ppm to about 1100 ppm; about 500 ppm to about 1200 ppm; about 500 ppm to about 1300 ppm; about 500 ppm to about 1400 ppm; or about 500 ppm to about 1500 ppm. In an aspect, the stabilizer component is present in an amount of about 1400 ppm to about 1500 ppm; about 1300 ppm to about 1500 ppm; about 1200 ppm to about 1500 ppm; about 1100 ppm to about 1500 ppm; about 1000 ppm to about 1500 ppm; about 900 ppm to about 1500 ppm; about 800 ppm to about 1500 ppm; about 700 ppm to about 1500 ppm; or about 600 ppm to about 1500 ppm. In an aspect, the stabilizer component is present in an amount greater than about 500 ppm; greater than about 550 pm; or greater than about 600 ppm. The stabilizer component can be present in an amount of about 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1,075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm.

In an aspect, a polymerization inhibitor component of a cyanoacrylate composition is a free radical stabilizer. Agents suitable for use as the polymerization inhibitor component include butylated hydroxy anisole (BHA); NMP (n-methyl-pyrrolidone), hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; and 2,2-methylene-bis-(4-methyl-6-tert-butylphenol), and the like, and mixtures thereof. In certain applications, the polymerization inhibitor component is BHA or BHT.

A polymerization inhibitor component can be present in an amount from about 4,000 ppm to about 7,000 ppm. In an aspect, a polymerization inhibitor component is present in an amount of about 4,000 ppm to about 4,500 ppm; 4,000 ppm to about 5,000 ppm; about 4,000 ppm to about 5,500 ppm; about 4,000 ppm to about 6,000 ppm; about 4,000 ppm to about 6,500 ppm; about 4,000 ppm to about 6,500 ppm; or about 4,000 ppm to about 7,000 ppm. In an aspect, a polymerization inhibitor component is present in an amount of about 4,500 ppm to about 7,000 ppm; about 5,000 ppm to about 7,000 ppm; or about 6,500 ppm to about 7,000 ppm. In an aspect, a polymerization inhibitor component is present in an amount greater than about 4,000 ppm; greater than about 4,500 pm; or greater than about 5,000 ppm. A polymerization inhibitor component can be present in an amount of about 4,000 ppm, 4,250 ppm, 4,500 ppm, 4,750 ppm, 5,000 ppm, 5,250 ppm, 5,500 ppm, 5,750 ppm, 6,000 ppm, 6,250 ppm, 6,500 ppm, 6,750 ppm, or 7,000 ppm.

A biodegradable cyanoacrylate composition contemplated by the current disclosure may comprise additives necessary to impart the desired properties, including viscosity, color, X-ray opacity, and others. For example, compositions of the present disclosure may include at least one plasticizing agent that imparts flexibility to the delivered polymerized material. A plasticizing agent(s) preferably contain little or no moisture and should not significantly affect the polymerization of the composition. Suitable plasticizers are known in the art and include those disclosed in U.S. Pat. Nos. 2,784,127 and 4,444,933, the disclosures of which are incorporated herein by reference in their entirety. Examples of suitable plasticizers include, but are not limited to, tributyl citrate (TBC), acetyl tributyl citrate (ATBC), dimethyl sebacate, triethyl phosphate, tri(2-ethylhexyl) phosphate, tri(p-cresyl) phosphate, glyceryl triacetate, glyceryl tributyrate, diethyl sebacate, diisodecyl adipate (DIDA), dioctyl adipate (DICA), isopropyl myristate, butyl stearate, lauric acid, trioctyl trimellitate, dioctyl glutarate (DICG), dioctyl phthalate, acetyl tri-n-butyl citrate, and the like, and mixtures thereof. In an aspect, suitable plasticizers may include polymeric plasticizers, such as polyethylene glycol (PEG) esters and capped PEG esters or ethers, polyester glutarates and polyester adipates. In an aspect, a plasticizer can be butyl benzyl phthalate, dibutyl phthalate, diethyl phthalate, dimethyl phthalate, dioctylphthalate, trialkyl acylcitrates, benzoate esters of di- and poly-hydroxy branched aliphatic compounds, tri(p-cresyl) phosphate, combinations thereof and the like. In an aspect, plasticizers can be acyl trialkyl citrates independently having from 1 to 10 carbon atoms in each alkyl group. For example, acyl trialkyl acylcitrates can be trimethyl O-acetylcitrate, triethyl O-acetylcitrate, tri-n-propyl O-acetylcitrate, tri-n-butyl O-acetylcitrate, tri-n-pentyl O-acetylcitrate, tri-n-hexyl O-acetylcitrate, tri-methyl O-propionylcitrate, tri-ethyl O-propionylcitrate, tri-n-propyl O-propionylcitrate, tri-n-butyl O-propionylcitrate, tri-n-pentyl O-propionylcitrate, tri-n-hexyl O-propionylcitrate, tri-methyl O-butyrylcitrate, tri-ethyl O-butyrylcitrate, tri-n-propyl O-butyrylcitrate, tri-n-butyl O-butyrylcitrate, tri-n-pentyl O-butyrylcitrate, tri-n-hexyl O-butyrylcitrate, and the like. In an aspect, the plasticizer can tri-n-butyl O-acetylcitrate. In an aspect, tributyl citrate, diisodecyl adipate and acetyl tributyl citrate, which when present are in an amount of up to thirty percent (30%) by weight of the liquid adhesive composition. The amount to be used can be determined by one of ordinary skills in the art, using known techniques without undue experimentation.

Compositions of the present disclosure may include at least one biocompatible agent effective in reducing active formaldehyde concentration levels during degradation (for compositions subject to in vivo degradation; such compounds are referred to as "formaldehyde concentration reducing agents"). Examples of formaldehyde scavenger compounds useful in this disclosure include, but are not limited to, the following: sulfites, bisulfites, ammonium sulfite salts, amines, amides, imides, nitriles, carbamates, alcohols; mercaptans, proteins, active methylene compounds such as cyclic ketones and compounds having a b-dicarbonyl group, certain heterocyclic ring compounds, and the like, and mixtures thereof. Bisulfites and sulfites useful as the formaldehyde scavenger include alkali metal salts and ammonium salts. Examples of useful amines include the aliphatic and aromatic amines, such as aniline, benzidine, aminopyrimidine, toluene-di amine, triethylenediamine, diphenylamine, diaminodiphenylamine, hydrazines, hydrazide, and the like, and mixtures thereof. Suitable proteins include collagen, gelatin, casein, soybean protein, vegetable protein, keratin, glue, and the like, and mixtures thereof. Suitable amides include urea, cyanamide, acrylamide, benzamide, and acetamide. Suitable alcohols include phenols, 1,4-butanediol, d-sorbitol, and polyvinyl alcohol. Examples of suitable compounds having a b-dicarbonyl group include malonic acid, acetylacetone, ethylacetone, acetate, malonamide, diethylmalonate, or another malonic ester and the like, and mixtures thereof.

Biodegradable cyanoacrylate compositions of the present disclosure may contain one or more adjuvant substances, such as thickening agents, medicaments, or the like to improve the medical or veterinary utility for the particular application.

Suitable thickeners include, for example, polycyanoacrylates, polylactic acid, poly-1,4-dioxa-2-one, poly oxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, polymethyl methacrylate and copolymers of alkyl methacrylates, butadiene, and the like, and mixtures thereof. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate), and the like, and mixtures thereof. In an aspect, a thickener can include a partial polymer of cyanoacrylate as disclosed in U.S. patent application Ser. No. 12/214,791, and triblock copolymers of polyoxyalkylene as disclosed in U.S. patent application Ser. No. 12/214,794. In many applications, it is desirable that the thickening agent is miscible in cyanoacrylate monomer compositions at room temperature.

In an aspect, a biodegradable cyanoacrylate composition, with or without a thickening agent, has a viscosity such that the liquid composition stops flowing beyond the intended application site or is substantially prevented from dripping. For example, a composition disclosed herein may have a viscosity of less than 100 cP, less than 50 cP, less than 30 cP, less than 20 cP, less than 15 cP, or the viscosity in the range of from about 10 cps to about 20 cP, from about 10 cP to about 30 cP, or from about 20 cP to about 30 cP, from about 10 cP to about 40 cP, from about 20 cP to about 40 cP. Standards and devices are known for measuring viscosity, such a viscometer, and cone and plate. As the biodegradable cyanoacrylate composition is provided pre-mixed and sterile, the initial biodegradable cyanoacrylate composition may have a lower viscosity than does a biodegradable cyanoacrylate composition after sterilization or a biodegradable cyanoacrylate composition during its usable period and/or nearing the end of its shelf-life. For example, an initial mixed sterilized biodegradable cyanoacrylate composition may have a viscosity that is less than or equal to 19 cP, or less than or equal to 18 cP, or less than or equal to 17 cP, less than or equal to 16 cP, or less than or equal to 15 cP, whereas a mixed sterilized biodegradable cyanoacrylate composition after a time during its usable shelf-life may have a viscosity that is less than or equal to 30 cP, or less than or equal to 29 cP, or less than or equal to 28 cP, less than or equal to 27 cP, or less than or equal to 26 cP, less than or equal to 25 cP, less than or equal to 24 cP, less than or equal to 23 cP, less than or equal to 22 cP, less than or equal to 21 cP, less than or equal to 20 cP.

Many known cyanoacrylate compositions have components that must be kept separated until the moment of use. For example, many adhesives require that two components be mixed and then immediately used as polymerization occurs at the point of mixing and application of the composition must occur before the polymerization is rapidly completed. This requires provision of ampules or separate containers for the components, to prevent polymerization in the containers provided.

Unlike these cyanoacrylate compositions, biodegradable cyanoacrylate compositions disclosed herein are provided in a mixed state, such that the biodegradable cyanoacrylate composition is provided in one container wherein the cyanoacrylate component, along with the other components such as the stabilizing component and the polymerization inhibitor component, are provided in one container and no mixing to initiate polymerization needs to be performed by the user before providing the biodegradable cyanoacrylate composition to the target site. The cyanoacrylate component may comprise one or more cyanoacrylate monomers therein. This mixed condition of the disclosed compositions may also be referred to herein as "pre-mixed" in contrast to cyanoacrylate compositions that must be immediately mixed at time of use to initiate polymerization. As can be understood, should a user wish to add components to the biodegradable cyanoacrylate composition, such as sonolucent particles, the particles may be mixed into the biodegradable cyanoacrylate composition, but this mixing is not performed to initiate polymerization of the cyanoacrylate monomers.

In an aspect, biodegradable cyanoacrylate compositions disclosed herein may be provided in a liquid state by providing a composition in containers, such as the containers disclosed herein. As referred to herein, disclosed biodegradable cyanoacrylate compositions are formulated by, for example, admixing two cyanoacrylate monomers, and the composition remains liquid, in an unpolymerized state, during shipping and storage until use. The biodegradable cyanoacrylate composition remains in a liquid state until application to a moisture-containing environment, such as a body lumen or surface. The disclosed biodegradable cyanoacrylate compositions have an extended shelf-life, during which time the composition meets the criteria and standards for use. For example, a biodegradable cyanoacrylate composition disclosed herein may have a shelf life of 0.5 year or longer, of 0.6 year or longer, of 0.7 year or longer, of 0.8 year or longer, of 0.9 year or longer, of 1.0 year or longer, or 1.2 year or longer, or 1.5 year or longer. For example, a biodegradable cyanoacrylate composition disclosed herein may have a shelf life of 0.5 year, 0.7 year, 0.9 year, 1.0 year, 1.2 year, or 1.5 year. The biodegradable cyanoacrylate composition may adequately function for longer periods than healthcare regulations permit for the provision of the compositions. To improve cohesive strength of a formed biodegradable cyanoacrylate composition, crosslinking agents known in the art may be added. Reference is made to U.S. Pat. No. 3,940,362 which is hereby incorporated by reference herein.

For certain applications, a biodegradable cyanoacrylate composition may further contain small amounts of colorants such as dyes or pigments. Suitable dyes include derivatives of anthracene and other complex structures, specifically, without limitation, 1-hydroxy-4-[4-methylphenylamino]-9, 10 anthracenedione (D&C violet No. 2); 9-(ocarboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2-(1,3 dihydro-3-oxo-5-sulfo-2H-indole-2-ylidine)-2,3-dihydro-3oxo-1H-ind-ole-5 sulfonic acid disodium salt (FD&C Blue No. 2); and 1,4-bis(4-methylanilino)anthracene-9,10-dione (D&C Green No. 6). In an aspect, the dyes are D&C Violet No. 2, FD&C Blue No. 2, and D&C Green No. 6.

In an aspect, a biodegradable cyanoacrylate composition may comprise sonolucent or radiopaque compounds or particles so that the occlusion can be monitored by sonography, fluoroscopy, or x-ray techniques.

In an aspect, a biodegradable cyanoacrylate composition can further comprise additional stabilizing or preservative agents such as alkyl parabens and salts thereof, ethylparaben, methylparaben, methylparaben sodium, propylparaben sodium, propylparaben, butylparaben, and the like. Other suitable preservatives include hydroquinone, pyrocatechol, resorcinol, 4-n-hexyl resorcinol, benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, cresols, phenylmercuric compounds such as phenylmercuric borate, and phenylmercuric nitrate.

In an aspect, a biodegradable cyanoacrylate composition can further comprise an antimicrobial agent in an effective amount. Suitable antimicrobial agents include antibacterial agents such as chlorhexidine and its salts, typical antibiotics, copolymers of vinylpyrrolidone and vinyl acetate, antiseptics, the iodine containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores and zephiran, copolymers of vinylpyrrolidone and vinyl acetate cross-linked with polyisocyanates, heavy metal salts such as silver nitrate, and aldehyde compounds such as glutaraldhyde.

For certain applications, a biodegradable cyanoacrylate composition may additionally contain polymerization initiators or accelerators that are activated by heat, light, or other modification on delivery to the site of action. Such initiators and accelerators are known in the art. Reference is made to U.S. Pat. No. 6,143,805 which is hereby incorporated by reference herein. For example, polymerization accelerators may be selected from calixarenes and oxacalixarenes, silacrowns, crown ethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,Ndimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives.

In an aspect, a crown ether as the accelerator may be included in a cyanoacrylate composition. Examples of crown ethers include, but are not limited to, 15-crown-5, 18-crown-6, dibenzo-18-crown-6, tribenzo-18-crown-6, dicyclohexyl-18-crown-6, benzo-1 5-crown5, dibenzo-24-crown-8, dibenzo-30-crown-10, asym-dibenzo-22-crown-6, dimethylsila-11 crown-4, dimethylsila-14-crown-5, dimethylsila-17-crown-6, dibenzo-14-crown-4, dicyclohexyl24-crown-8, asym-dibenzo-22-crown-6, cyclohexyl-12-crown-4,1,2-decalyl-15-crown-5,1,2-naphtho-1 5-crown-5,3,4,5-naphthyl-16-crown-5,1,2-methyl-benzo-18-crown-6,1,2-methylbenzo-5,6-methylbenzo-18-crown-6,1,2-t-butyl-18-crown-6,1,2-vinylbenzo-15-crown-5,1,2-vinylbenzo-18-crown-6,1,2-t-butyl-cyclohexyl-18-crown-6, and 1,2-benzo-1,4-benzo-5oxygen-20-crown-7.

In an aspect, the amount of polymerization accelerator that is added to a cyanoacrylate composition is in the amount of about 10 ppm-6000 ppm. For example, the polymerization accelerator can be present in the amount of about 40 ppm-5000 ppm, and more preferably about 60 ppm-4000 ppm of the liquid adhesive composition. The amount of polymerization accelerator to be used can be determined by one of ordinary skill in the art using known techniques without undue experimentation.

Though not wishing to be bound by any particular theory, it is believed that disclosed biodegradable cyanoacrylate compositions induce a cellular and/or tissue reaction in two layers of a conduit, for example, to both the epithelial layer and to the myosalpinx (muscular layer) of a body conduit, such as a fallopian tube. The cellular and/or tissue reaction induced by chemical and physical contact of the polymerized cyanoacrylate composition with these body layers may occur over a duration of weeks to several months. While it performs its function of a prolonged reaction to the tissues over time, the biodegradable cyanoacrylate composition gradually degrades. Though not wishing to be bound by any particular theory, it is thought that the degradation process begins at the interface of the solidified (polymerized) composition and the epithelial layer. Over time, chemical bonds of the polymerized composition at the epithelial layer will be continually exposed to moisture and secretions generated by the secretary cells of the mucosa. The exposure leads to a gradual breakdown and removal of the polymerized composition. Along with degradation and expulsion of the polymerized composition, the exposed and reacting muscle layers of the conduit, for example those on opposing sides of the conduit, come into direct contact with each other, and in healing, anneal together to form a lasting occlusion and close off the conduit. The polymerized cyanoacrylate forms the initial occlusion of the conduit, and though the cyanoacrylate composition degrades and leaves the conduit, the affected tissue forms the lasting occlusion.

Though not wishing to be bound by any particular theory, it is believed that a cyanoacrylate composition disclosed herein is primarily degraded by ester hydrolysis. For example, methoxypropyl cyanoacrylate was found by Shalaby and Shalaby (Chapter 5, Cyanoacrylate-based Systems as Tissue Adhesives. Absorbable and Biodegradable Polymers, 2004. CRC Press LLC) to be a more hydrophilic cyanoacrylate than cyanoacrylates that degrade by the chain scission degradation pathway. Methoxypropyl cyanoacrylates under hydrolysis of their ester group, produce water-soluble by-products, without formation of formaldehyde. Polymerization of methoxypropyl cyanoacrylate is based on hydrolysis of chain pendent ester groups and formation of water-soluble, excretable by-products. Some by-products are alcohols, with no detectable acetate production and/or very low levels of formaldehyde.

A biodegradable cyanoacrylate composition may be placed into and stored in a container, including, but not limited to containers made of plastic, aluminum or glass. Examples of containers include, but not are not limited to, pouches, vials, applicators such as swabs or an applicator tip on a container holding a composition therein, ampoules, syringes, pipettes, and components of medical devices capable of delivering the cyanoacrylate composition.

An article of the present disclosure comprises a container containing a biodegradable cyanoacrylate composition disclosed herein. For example, an article (container containing a biodegradable cyanoacrylate composition disclosed herein) may be a component of a medical device. Such a medical device container component may be sterilized so that the cyanoacrylate composition contained therein is also sterilized. Cyanoacrylate compositions of the present disclosure are capable of being contained for a certain amount of time in an unpolymerized state, and when applied to a body surface, such as a mucous membrane, polymerization of the cyanoacrylate monomers proceeds.

Such an article, a container of a disclosed biodegradable cyanoacrylate composition, may be provided in a kit with a medical device. A kit of the present disclosure comprises an article containing a disclosed biodegradable cyanoacrylate composition and a medical device, for example, a medical device capable of delivering the biodegradable cyanoacrylate composition. Optionally, the article is accompanied by a desiccant. A desiccant may be provided in its container. For example, a desiccant may be a silica gel or other known desiccant capable of absorbing moisture for at least the shelf-life period of time for the biodegradable cyanoacrylate composition. Silica gel is a granular, vitreous, porous form of silicon dioxide made synthetically from sodium silicate. Most applications of silica gel require it to be dried, in which case it is called silica xerogel. For practical purposes, silica gel is often interchangeable with silica xerogel. A molecular sieve is another example of a desiccant-like material to be provided with a container of a biodegradable cyanoacrylate composition.

A desiccant may be provided in any suitable container. For example, the desiccant may be provided in a pouch made from a sheet of polyethylene fibers having a high wet strength and permeable to both gases and odors. An example is Tyvek®, by DuPont, and appropriate desiccants are available commercially, from, for example, Sigma-Aldrich, St. Louis, MO 63178, USA. For example, a pouch may contain 1 gram of desiccant, which may adsorb a minimum of 25% its weight or 0.25 g.

In an aspect, a container of a biodegradable cyanoacrylate composition disclosed herein comprises a container comprising a polymeric material. For example, such a container may be made from, or at least lined with, a polypropylene (PP) heterophasic block copolymer. Such a material is available from Borealis, Wagramer Strasse 17-19, 1220 Vienna, Austria. A disclosed biodegradable cyanoacrylate composition may be provided in a polypropylene or polypropylene copolymer cylindrical container, similar to a syringe body, having plungers and optionally a cap to close the other end of the syringe body. A plunger may be made of, or at least the portion(s) that would contact the biodegradable cyanoacrylate composition, made of a material that does not adhere to the biodegradable cyanoacrylate composition and does not cause the biodegradable cyanoacrylate composition to initiate polymerization or degrade. For example, the plunger and/or its contacting portion may be made from a plastic, for example PTFE. The cap closure of the opposing end of a container (e.g., a syringe outlet) may be made of a material that does not adhere to the biodegradable cyanoacrylate composition and does not cause the biodegradable cyanoacrylate composition to initiate polymerization or degrade. For example, the cap closure and/or its contacting portion may be made from a plastic, for example HDPE.

In embodiments, the container enclosing the composition can be of single-layer or of multi-layer construction of various materials. In an aspect, an inner most layer in contact with biodegradable cyanoacrylate composition is composed of a polymer or copolymer. The single-layer or multi-layer construction of the container may be any combination of any material suitable for storage and delivery of a liquid adhesive composition. By way of example, suitable materials include polymers, copolymers, thermoplastic polymers, plastics, nitrile polymers and copolymers, and metal, such as foil.

Suitable thermoplastic polymers include the polyolefins, which include but are not limited to polyethylene (PE), and polypropylene (PP), and polyesters, such as, polyethylene terephthalate (PET). Any class of polyethylenes are suitable, including high density polyethylene (HDPE), high density cross-linked polyethylene (HDXLPE), cross-linked polyethylene (XLPE), medium density polyethylene (MDPE), linear low density polyethylene (LLDPE), low density polyethylene (LDPE), and very low density polyethylene (VLDPE), high molecular weight polyethylene (HMWPE), ultra low molecular weight polyethylene (ULMWPE) and ultra high molecular weight polyethylene (UHMWPE). A biodegradable cyanoacrylate composition disclosed herein may be provided in a suitable container, wherein suitable means a container that does not cause or allow the biodegradable cyanoacrylate composition to polymerize prior to providing the biodegradable cyanoacrylate composition to a moisture-containing environment.

A biodegradable cyanoacrylate composition is placed within its suitable container. Though not wishing to be bound by any particular theory, it is believed by some that cyanoacrylate compositions are self-sterilizing, in that they do not need to undergo sterilizing conditions to be safe and effective for use in a living body. The present disclosure contemplates biodegradable cyanoacrylate compositions that have and have not undergone sterilizing conditions. For healthcare regulations, generally, biodegradable cyanoacrylate compositions disclosed herein are provided after undergoing sterilizing conditions. For example, after being placed in a suitable container, the container containing the biodegradable cyanoacrylate composition is then sterilized.

In an aspect, a biodegradable cyanoacrylate composition comprises a cyanoacrylate component comprising a one cyanoacrylate compound or monomer or a blend or admixture of cyanoacrylate compounds or monomers, referred to herein as a cyanoacrylate or cyanoacrylates. For example, a cyanoacrylate component may comprise one cyanoacrylate or more than one cyanoacrylate in a blend or admixture of cyanoacrylates. A cyanoacrylate component of the present disclosure may comprise one or more cyanoacrylates that have long side groups, relatively slow polymerization and slow degradation, in comparison to methyl-2-cyanoacrylate, which has a short side group, fast polymerization and fast degradation, and in comparison to a blend of 2-octyl cyanoacrylate and butyl lactoyl cyanoacrylate, which has a long side group, slow polymerization and very slow degradation.

In an aspect, a biodegradable cyanoacrylate composition consists of a cyanoacrylate component consisting of 30 wt % (±5%) 2-butyoxyethyl cyanoacrylate and 70 wt % (±5%) pentyl cyanoacrylate, a stabilizing component consisting of lactone, in an amount from amount from about 500 ppm to about 700 ppm, and a polymerization inhibitor component consisting of dinitrophenol, in an amount from about 4000 ppm to 6000 ppm.

In an aspect, a biodegradable cyanoacrylate composition consists of a cyanoacrylate component consisting of 60 wt % (±5%) nonyl cyanoacrylate and 40 wt % (±5%) 2-octyl cyanoacrylate, a stabilizing component consisting of carbonic acid, in an amount from amount from about 400 ppm to about 800 ppm, and a polymerization inhibitor component consisting of hydroquinone, in an amount from about 4000 ppm to 6000 ppm.

In an aspect, a biodegradable cyanoacrylate composition consists of a cyanoacrylate component consisting of 50 wt % (±5%) n-butyl-2-cyanoacrylate and 50 wt % (±5%) septyl cyanoacrylate, a stabilizing component consisting of sulfur dioxide, in an amount from amount from about 400 ppm to about 800 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 50 wt % (±5%) methoxy-n-propyl cyanoacrylate and 50 wt % (±5%) methoxy-iso-propyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 30 wt % (±5%) methoxy-n-propyl cyanoacrylate and 70 wt % (±5%) methoxy-iso-propyl cyanoacrylate, a stabilizing component consisting of sulfur dioxide, in an amount from amount from about 600 ppm to about 700 ppm, and a polymerization inhibitor component consisting of butylated hydroxyanisole, in an amount from about 5000 ppm to 6000 ppm.

In an aspect, a biodegradable cyanoacrylate composition consists of a cyanoacrylate component consisting of 70 wt % (±5%) methoxy-n-propyl cyanoacrylate and 30 wt % (±5%) methoxy-iso-propyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 6000 ppm.

In an aspect, a biodegradable cyanoacrylate composition consists of a cyanoacrylate component consisting of 40 wt % (±5%) 2-isopropoxethyl cyanoacrylate and 60 wt % (±5%) pentyl cyanoacrylate, a stabilizing component consisting of acetic acid, in an amount from amount from about 600 ppm to about 700 ppm, and a polymerization inhibitor component consisting of butylated hydroxyanisole, in an amount from about 5000 ppm to 7000 ppm.

In an aspect, a biodegradable cyanoacrylate composition comprises a cyanoacrylate component consisting of greater than 95 wt %, or greater than 99 wt %, of methoxypropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising greater than 95 wt %, or greater than 99 wt %, of methoxypropyl cyanoacrylate, a stabilizing component comprising sulfur dioxide, in an amount from amount from about 500 ppm to about 700 ppm, and a polymerization inhibitor component comprising butylated hydroxyanisole, in an amount from about 4000 ppm to 7000 ppm.

In an aspect, a biodegradable cyanoacrylate composition consists of a cyanoacrylate component consisting of greater than 95 wt %, or greater than 99 wt %, of methoxypropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component consisting of greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprises greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole (BHA), in an amount from about 4000 ppm to 7000 ppm.

In an aspect, a biodegradable cyanoacrylate composition consists of a cyanoacrylate component consisting of greater than 95 wt %, or greater than 99 wt %, of methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 70 wt % (±5%) methoxypropyl cyanoacrylate and 30 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 70 wt % (±5%) methoxypropyl cyanoacrylate and at least 30 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 30 wt % (±5%) methoxypropyl cyanoacrylate and 70 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 30 wt % (±5%) methoxypropyl cyanoacrylate and at least 70 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 50 wt % (±5%) methoxypropyl cyanoacrylate and 50 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition comprises a cyanoacrylate component comprising at least 50 wt % (±5%) methoxypropyl cyanoacrylate and at least 50 wt % (±5%) methoxyisopropyl cyanoacrylate, a stabilizing component consisting of sulfur dioxide, in an amount from amount from about 500 ppm to about 700 ppm, and a polymerization inhibitor component consisting of butylated hydroxyanisole, in an amount from about 4000 ppm to 7000 ppm.

In an aspect, a biodegradable cyanoacrylate composition consists of a cyanoacrylate component consisting of 60 wt % (±5%) 2-isopropoxethyl cyanoacrylate and 40 wt % (±5%) pentyl cyanoacrylate, a stabilizing component consisting of acetic acid, in an amount from amount from about 600 ppm to about 700 ppm, and a polymerization inhibitor component consisting of catechol, in an amount from about 5000 ppm to 7000 ppm.

In an aspect, a biodegradable cyanoacrylate composition consists of a cyanoacrylate component consisting of 50 wt % (±5%) 2-isopropoxethyl cyanoacrylate and 50 wt % (±5%) pentyl cyanoacrylate, a stabilizing component consisting of acetic acid, in an amount from amount from about 600 ppm to about 700 ppm, and a polymerization inhibitor component consisting of catechol, in an amount from about 5000 ppm to 7000 ppm.

A biodegradable cyanoacrylate composition disclosed herein can be defined by functional characteristics. A biodegradable cyanoacrylate composition suitable for methods of conduit occlusion in human and animals comprises a composition that passes on or all biocompatibility characterizing tests, for example, as measured by ISO standards, and fails cytotoxicity testing, for example, as measured by ISO 10993-5:2009. Biodegradable cyanoacrylate compositions of the present disclosure comprise a cyanoacrylate component, a stabilizing component and a polymerization inhibitor component and passes two or more biocompatibility tests for sensitization (for example, as measured by ISO 10993-10:2010), irritation (for example, as measured by ISO 10993-10:2010), vaginal irritation (for example, as measured by ISO 10993-10:2010), pyrogenicity (for example, as measured by ISO 10993-11:2010), systemic acute toxicity (for example, as measured by ISO 10993-11:2010), systemic sub-chronic toxicity (for example, as measured by ISO 10993-11:2010), genotoxicity (for example, as measured by ISO 10993-3:2003), rodent blood micronucleus assay (for example, as measured by ISO 10993-3:2003), and mouse lymphoma mutagenesis (for example, as measured by ISO 10993-3:2003), and fails cytotoxicity testing (for example, as measured by ISO 10993-5:2009). Compositions used for human or animal treatments must pass these listed biocompatibility tests to be considered safe for use, thus in an aspect, a disclosed biodegradable cyanoacrylate composition must pass each of these tests (sensitization, irritation, vaginal irritation, pyrogenicity, systemic acute toxicity, systemic sub-chronic toxicity, genotoxicity, rodent blood micronucleus assay, and mouse lymphoma mutagenesis, and fail the cytotoxicity test.

A composition disclosed herein, for example, for conduit occlusion, comprises a cyanoacrylate component, a stabilizer component and a polymerization inhibitor component and fails cytotoxicity testing, for example, as measured by ISO 10993-5:2009, and passes biocompatibility testing for genotoxicity, for example, as measured by ISO 10993-3:2003. A composition for conduit occlusion comprises a cyanoacrylate component, a stabilizer component and a polymerization inhibitor component and fails cytotoxicity testing, for example, as measured by ISO 10993-5:2009, and passes at least biocompatibility testing for genotoxicity, for example, as measured by ISO 10993-3:2003.

In an aspect, a biodegradable cyanoacrylate composition disclosed herein has a low heat of polymerization, for example, compared to a known cyanoacrylate composition, Histoacryl. Histoacryl, available from commercial suppliers such as Aesculap AG, Am AESCULAP-Platz, D-78532 Tuttlingen/Donau, AT, is a cyanoacrylate composition comprising butyl cyanoacrylate. In an example, using a pig skin pouch to simulate a body conduit, the increase in temperature (herein the heat of polymerization) found after administration of the biodegradable cyanoacrylate composition to the pig skin was less than 1° C. (i.e., at approximately 0.7° C.), whereas the increase in temperature (herein the heat of polymerization) of Histoacryl was 6.7° C. In an aspect, a composition disclosed herein, for example, for conduit occlusion, comprises a cyanoacrylate component, a stabilizer component and a polymerization inhibitor component and has a low heat of polymerization temperature of less than 6° C., of less than 5° C., of less than 4° C., of less than 3° C., of less than 2° C., of less than 1° C., or in a range from about 0.5° C. to about 6° C., and all ranges therein between. In an aspect, a biodegradable cyanoacrylate composition disclosed herein, for example, for conduit occlusion, comprises a cyanoacrylate component, a stabilizer component and a polymerization inhibitor component and has a low heat of polymerization temperature in a range of from 0.5° C. to 1.0° C. Heat of polymerization may be measured by differential scanning calorimetry, for example, based on ASTM D3418-12e1.

In an aspect, a biodegradable cyanoacrylate composition disclosed herein, for example, for conduit occlusion, comprises a cyanoacrylate component, a stabilizer component and a polymerization inhibitor component, that has a rapid in vitro cure time or setting time but does not release deleterious heat. Cure time or setting time refers to the rate of polymerization of at least a portion of the composition. For example, biodegradable cyanoacrylate compositions disclosed herein were tested in pig fallopian tubes and a complete curing of the administered biodegradeable cyanoacrylate composition was seen at 2 minutes. In an aspect, a biodegradable cyanoacrylate composition disclosed herein has a cure time of at least a portion of the administered composition of greater than or equal to 10 seconds, of greater than or equal to 15 seconds, of greater than or equal to 20 seconds, of greater than or equal to 30 seconds, of greater than or equal to 40 seconds, of greater than or equal to 50 seconds, of greater than or equal to 60 seconds, of greater than or equal to 70 seconds, of greater than or equal to 80 seconds, of greater than or equal to 90 seconds, of greater than or equal to 100 seconds, of greater than or equal to 110 seconds, or of greater than or equal to 120 seconds. In an aspect, biodegradable cyanoacrylate composition disclosed herein has a cure time of 2 minutes or less, of less than 110 seconds, of less than 100 seconds, of less than 90 seconds, of less than 80 seconds, of less than 70 seconds, of less than 60 seconds, of less than 50 seconds, of less than 40 seconds, of less than 30 seconds, of less than 25 seconds, of less than 20 seconds, of less than 15 seconds, or of less than 10 seconds. In an aspect, a biodegradable cyanoacrylate composition disclosed herein has a cure time (or setting time) of between 10 seconds and 120 seconds.

In an aspect, a biodegradable cyanoacrylate composition disclosed herein is pliable when polymerized. Pliability may be assessed by a free-bend test, wherein a composition is polymerized into a rod and the rod is bent 180°. The extent of damage or change is documented by fracture, surface condition and cracking of the rod. In an experiment, a polymerized rod of a disclosed biodegradable cyanoacrylate composition was compared to a polymerized rod of Histoacryl Blue (butyl cyanoacrylate), the disclosed biodegradable cyanoacrylate composition bent 180 degrees without damage or significant change whereas the Histoacryl Blue rod broke in pieces before reaching 180 degrees of bending. In an aspect, a biodegradable cyanoacrylate composition disclosed herein is pliable, as measured by this test, after polymerization.

In an aspect, a biodegradable cyanoacrylate composition disclosed herein, for example, for conduit occlusion, comprises a cyanoacrylate component, a stabilizer component and a polymerization inhibitor component, that passes at least a biocompatibility test for genotoxicity, fails a biocompatibility test for cytotoxicity, has a low heat of polymerization temperature in a range of from 0.5° C. to 1.0° C., has a viscosity of less than or equal to 30 cP, a cure or setting time between 10 seconds and 30 seconds, is pliable, and a shelf-life of greater than 0.5 year, and optionally, the composition may be sterilized.

Biodegradable cyanoacrylate compositions of the present disclosure are suitable for use in medical and veterinary applications. Biodegradable cyanoacrylate compositions for such applications are preferably sterile. Thus, the present disclosure comprises sterile biodegradable cyanoacrylate compositions as described herein. Biodegradable cyanoacrylate compositions disclosed herein may be sterilized by common techniques. Sterilization of the cyanoacryolate adhesive compositions is accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods of sterilization are chemical sterilization and electron beam sterilization. For example, a suitable container containing a disclosed biodegradable cyanoacrylate composition may be sterilized by 10-20 kGy does electron beam processing. Such sterilization methods are known in the art, and for example, taught by ISO 11137-2. In general, methods of the present disclosure comprise providing and/or administering or applying biodegradable cyanoacrylate compositions, comprising at least a cyanoacrylate component, a stabilizer component and a polymerization inhibitor component, to site on or in a body, for example, in or near a conduit for occluding a conduit. In an aspect, disclosed herein are exemplary compositions for occlusion of conduits, for example, of the reproductive tracts of mammals. Such compositions can be used in other physiological systems and biological sites of humans or other animals, whether such sites are naturally there or have been created, for example, by surgical means, and such uses are contemplated by the present disclosure.

One aspect of the present disclosure comprises methods of contraception for mammalian females that administer a biodegradable cyanoacrylate composition to a target site, for example, from the cornual aspect of the uterus into each fallopian tube, wherein the biodegradable cyanoacrylate composition is capable of creating an occlusion in each fallopian tube.

One area that has a need for occlusion of a body tube is the control of fertility by occlusion of the fallopian tubes. It is well known in the art that a primary cause of naturally occurring infertility in females is blockage of the oviducts from the ovary to the uterus. Females having this natural condition normally do not even realize it exists and do not suffer any adverse side effects besides being infertile.

Based upon the observations of naturally occurring oviductal occlusion, the creation of tubal occlusions by external intervention is an effective means of causing female sterilization. In the early 1980's a cyanoacrylate composition of methyl cyanoacrylate was utilized for female sterilization by occluding the fallopian tubes. In order to stabilize this highly reactive cyanoacrylate, high levels of acids were utilized. This composition was never made commercially viable due to the difficulty in handling of the methyl cyanoacrylate material, lower than acceptable effectiveness rates, and the need to use multiple applications of the methyl cyanoacrylate material.

Utilizing occluding compositions to create an occlusion in the fallopian tubes would be ideal if it could be delivered non-surgically through intrauterine catheters, such as those described in U.S. Pat. Nos. 8,048,086; 8,048,101; 8,052,669; 8,316,853; 8,316,854; 8,336,552; 8,324,193; 8,695,606; 9,034,053; 8,726,906; 9,220,880, and applications claiming priority thereto, each of which is herein incorporated in its entirety. Non-surgical options to achieve permanent sterilization are limited and involve permanent implants being deposited into the fallopian tubes to create the long-term occlusion. Use of quinacrine is well established to create scarring of the tubal epithelium and cause tubal blockage but has significant limitations in that it is not containable to the conduit, allowing for spillage to the peritoneal cavity.

For example, in an aspect a method comprises delivering, using a catheter or delivery system comprising one or more catheters, into the uterine cavity cornua, and directed to the fallopian tubes, a liquid biodegradable cyanoacrylate composition. An effective amount of a biodegradable cyanoacrylate composition disclosed herein is delivered, and may comprise from about 0.3 to 1.0 mL of liquid cyanoacrylate composition, or 0.3, 0.4, 0.5, 0.6, 0.7, 0.8, 0.9, 1.0 mL may be delivered. Larger or smaller amounts may be delivered, but the method is not contemplated to fill the entire fallopian tube, but to deliver minimally, for example, to the interstitial (intramural) portion of the tube and to form an occlusion in the proximal portion of the fallopian tube. The biodegradable cyanoacrylate composition polymerizes (solidifies) upon contact with the tissue and fluids in the uterine cavity and fallopian tube(s). It is believed that the biodegradable cyanoacrylate composition adheres primarily to the epithelial lining of the corneal region and luminal circumference due to chemical bonding and physical contact of the polymerized cyanoacrylate composition. The biodegradable cyanoacrylate composition occupies spaces within the undulating structure of the epithelium.

It is believed that the biodegradable cyanoacrylate composition is substantially confined to the target areas during and after the polymerization process. This may be due, in part, to delivering the cyanoacrylate composition in a controlled, (e.g., slow) manner and in a discrete volume. One of skill in the art would understand how to deliver a polymerizable composition.

It is believed that a disclosed biodegradable cyanoacrylate composition induces cellular and/or tissue inflammatory-type reactions in both the epithelial lining and to the myosalpinx (muscular layer) of the fallopian tube. The cellular and/or tissue reaction is induced by chemical and physical contact with the tubal lining circumference and may last for several weeks. Prolonged cellular and/or tissue reaction prevents typical regeneration healing actions that could occur for shorter durations of cell injury, especially in the myosalpinx which regenerates more slowly than the endosalpinx. Without typical fibrinolysis that repairs short term inflammation, the reacting tissues will not heal with functional tissue, and instead, formation of nonfunctional scar tissue takes place. While the polymerized biodegradable cyanoacrylate composition is providing a prolonged reaction to the tissues over several weeks, the biodegradable cyanoacrylate composition is gradually degrading. It is thought that with time, the surface bonds of the polymerized biodegradable cyanoacrylate composition will be continually exposed to moisture and secretions generated by secretory cells of the mucous membrane. This exposure leads to a gradual breakdown and removal of the biodegradable cyanoacrylate composition. Once the biodegradable cyanoacrylate composition is removed from an area of the fallopian tube, occlusion occurs by luminal obliteration and scarring. It is expected that as the polymerized biodegradable cyanoacrylate composition degrades, the degradation products and/or solid pieces of the polymerized material which break off, will travel in the direction of the uterine cavity by the tubal fluid and by the pro-uterine ciliary beat, and then out the vagina.

In order to provide for successful occlusion of a fallopian tube with a biodegradable cyanoacrylate composition delivered through intrauterine catheters non-surgically, the following is desirable:

- a biodegradable cyanoacrylate composition that remains in liquid form when stored pre- and post-sterilization and during delivery, therefore, a biodegradable cyanoacrylate composition may be formulated to be stable and not undergo premature polymerization;
- a biodegradable cyanoacrylate composition may be of suitable viscosity to travel through and be delivered by intrauterine catheters directed at or into the target site, such as a fallopian tube(s);
- once delivered to the target site, such as a fallopian tube(s), a biodegradable cyanoacrylate composition may polymerize quickly, e.g., within a few seconds, to prevent movement from the target site, e.g., fallopian tubes;
- the resulting cured polymer (polymerized biodegradable cyanoacrylate composition material) may elicit a localized reaction, while the polymer begins to degrade, breakdown, and/or break apart;
- the resulting cured polymer (polymerized biodegradable cyanoacrylate material) may lack durability, shedding from the conduit over time allowing for a durable occlusion due to the conduit's response to the cyanoacrylate composition and its healing reaction; and
- a biodegradable cyanoacrylate composition is administered and the resulting cured composition is non-toxic and biocompatible for the subject to whom the occluding composition is provided, but may be deleterious to other cells such as sperm.

The biodegradable cyanoacrylate compositions may also be naturally sonolucent or may be modified to have enhanced sonolucency by the introduction of materials or bubbles such as microbubbles of air or gas. These microbubbles may be present within the composition or may be present when the composition polymerizes into a solid form.

A method disclosed herein comprises administering a biodegradable cyanoacrylate composition at or near the site for occlusion and allowing the cyanoacrylate composition to polymerize in situ in the site. A method may further comprise viewing the occluding site. A method may further comprise testing that occlusion of the site has occurred. Delivery methods for delivering a cyanoacrylate composition to one or more mammalian fallopian tubes are taught in U.S. Pat. Nos. 8,048,086; 8,048,101; 8,052,669; 8,316,853; 8,316,854; 8,336,552; 8,324,193; 8,695,606; 9,034,053; 8,726,906; 9,220,880, and applications claiming priority thereto, each of which is herein incorporated in its entirety. Methods for evaluating the fallopian tubes are known in the art and may include U.S. Pat. No. 9,554,826, and/or U.S. Ser. No. 13/292,990, each of which is herein incorporated in its entirety. In a method wherein two catheters are used for delivery of a biodegradable cyanoacrylate composition, two containers, for example, two syringes, of the same biodegradable cyanoacrylate composition can be provided.

Packaging and Sterilization

For compositions and methods disclosed herein, biodegradable cyanoacrylate compositions may be provided as sterile. It would be desirable if the sterilization techniques were conducted on a packaged composition so that, upon sterilization, the sterilized composition could be shipped as sterile. Compositions containing cyanoacrylate esters often polymerize rapidly, often beginning instantaneously, upon contact with tissue or fluid.

A biodegradable cyanoacrylate composition may be provided in a container that does not react with the biodegradable cyanoacrylate composition and does not cause premature polymerization, i.e., polymerization before the composition is provided to the target site. Examples of containers of suitable materials are disclosed herein.

Kits

The present disclosure comprises a kit comprising a biodegradable cyanoacrylate composition disclosed herein, contained within a container and optionally, further comprising a desiccant. The kit may further comprise written instructions for its use. Compositions disclosed herein may be provided in a kit with a medical device for delivering a biodegradable cyanoacrylate composition. Such kits also include written directions for use of the medical device and the biodegradable cyanoacrylate composition. A kit may comprise a biodegradable cyanoacrylate composition in a suitable container, optionally further comprising a desiccant, and a medical device for delivering the biodegradable cyanoacrylate composition and instructions for use of the composition and medical device.

Disclosed herein are compositions, methods, articles, kits and medical devices comprising biodegradable, cyanoacrylate compositions. A disclosed biodegradable cyanoacrylate composition comprises a) a cyanoacrylate component comprising at least one cyanoacrylate, wherein the cyanoacrylate component is 80 wt % or greater; b) a stabilizer component in a range from 500 ppm to 1500 ppm; and c) a polymerization inhibitor component in a range from 4000 to 7000 ppm. A disclosed biodegradable cyanoacrylate composition may comprise a biodegradable cyanoacrylate composition wherein the cyanoacrylate component comprises at least two cyanoacrylate monomers.

A disclosed biodegradable cyanoacrylate composition may comprise a biodegradable cyanoacrylate composition wherein the cyanoacrylate monomer is methyl cyanoacrylate, ethyl cyanoacrylate, propyl cyanoacrylate, butyl cyanoacrylate, pentyl cyanoacrylate, hexyl cyanoacrylate, septyl cyanoacrylate, octyl nonyl cyanoacrylate, decyl 2-cyanoacrylate, allyl cyanoacrylate, methoxyethyl cyanoacrylate, methoxyisopropyl cyanoacrylate, methoxypropyl cyanoacrylate, methoxybutyl cyanoacrylate, methoxypentyl cyanoacrylate, or combinations thereof.

A disclosed biodegradable cyanoacrylate composition may comprise a biodegradable cyanoacrylate composition wherein the stabilizer component comprises an alkyl sulfide, alkyl sulfate, alkyl sulfonyl, alkyl sulfone, alkyl sulfoxide, alkyl sulfite, sultone, sulfur dioxide, sulfur trioxide, sulfonic acid, lactone, boron trifluoride, acetic acid, or 3-sulfolene, mercaptan, or combinations thereof. A disclosed biodegradable cyanoacrylate composition may comprise a biodegradable cyanoacrylate composition wherein the stabilizer component comprises sulfur dioxide or sulfur trioxide.

A disclosed biodegradable cyanoacrylate composition may comprise a biodegradable cyanoacrylate composition wherein the polymerization inhibitor component comprises butylated hydroxy anisole (BHA); hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; or 2,2-methylene-bis-(4-methyl-6-tert-butylphenol), or combinations thereof. A disclosed biodegradable cyanoacrylate composition may comprise a biodegradable cyanoacrylate composition wherein the polymerization inhibitor component comprises BHA or BHT.

A disclosed biodegradable cyanoacrylate composition may comprise hydrogen sulfide, carbonic acid, triacetylmethane, acetic acid, benzoic acid, dinitrophenol, formic acid, nitrous acid, hydrochloric acid, hydrobromic acid, hydrofluoric acid, chloroacetic acid, phosphoric acid, dichloroacetic acid, trichloroacetic acid, trinitrophenol, trifluoroacetic acid, sulfuric acid, perchloric acid, toluenesulfonic acid, or fluorosulfonic acid, or combinations thereof.

A disclosed biodegradable cyanoacrylate composition may comprise a plasticizing agent, biocompatible agent, thickening agent, medicament, crosslinking agent, dye or pigment, preservative, antimicrobial agent, or polymerization initiator or accelerator. A disclosed biodegradable cyanoacrylate composition may comprise a biodegradable cyanoacrylate composition wherein the composition is sterile.

A disclosed biodegradable cyanoacrylate composition may comprise a biodegradable cyanoacrylate composition wherein the composition is contained in a container that is a component of a medical device.

A kit is disclosed wherein the kit comprises one or more of the biodegradable cyanoacrylate compositions disclosed herein. A kit may comprise a biodegradable cyanoacrylate composition that is sterile, meaning that the composition has been sterilized by procedures and methods disclosed herein.

A disclosed biodegradable cyanoacrylate composition comprises a) a cyanoacrylate component comprising at least one cyanoacrylate, wherein the cyanoacrylate component is 90 wt % or greater; b) a stabilizer component in a range from 500 ppm to 1500 ppm; and c) a polymerization inhibitor component in a range from 4000 to 7000 ppm.

A disclosed biodegradable cyanoacrylate composition comprises a) a cyanoacrylate component comprising at least one cyanoacrylate, wherein the cyanoacrylate component is 90 wt % or greater; b) a stabilizer component in a range from 500 ppm to 1500 ppm; and c) a polymerization inhibitor component in a range from 4000 to 7000 ppm, wherein the composition, under ISO test conditions, fails to pass a Neutral Red cytotoxicity test (as measured by ISO 10993-5:2009) and passes a biocompatibility test for at least genotoxicity (as measured by ISO 10993-3:2003). A disclosed biodegradable cyanoacrylate composition may comprise a biodegradable cyanoacrylate composition that fails the cytotoxicity test and passes each of the biocompatibility tests for sensitization (as measured by ISO 10993-10:2010), irritation (as measured by ISO 10993-10:2010), vaginal irritation (as measured by ISO 10993-10:2010), pyrogenicity (as measured by ISO 10993-11:2010), systemic acute toxicity (as measured by ISO 10993-11:2010), systemic sub-chronic toxicity (ISO 10993-11:2010), genotoxicity (as measured by ISO 10993-3:2003), rodent blood micronucleus assay (as measured by ISO 10993-3:2003), and mouse lymphoma mutagenesis (as measured by ISO 10993-3:2003).

A disclosed method for occluding one or more conduits in a subject may comprise administering a disclosed sterile biodegradable cyanoacrylate composition at or near the site for occlusion and maintaining the composition at the site so that the biodegradable cyanoacrylate composition polymerizes and provides a temporary polymerized occlusion in the conduit, and with time, the polymerized material is degraded and a cellular occlusion is formed at the site.

A component of a medical device may comprise a container containing a disclosed biodegradable cyanoacrylate composition. The component may comprise a component wherein the container, the biodegradable cyanoacrylate composition, or both are sterile.

Definitions

As used herein, the term "conduit" shall refer to any tube, duct, or passage, whether natural or synthetic, which carries gas, fluids or solids in a biological system.

As used herein, "occlude" refers to blocking, partially or fully, the transport of gas, fluids, or solids through a conduit. The term "occlusion," as used herein, refers to blockage within a conduit wherein such blockage results in partial restriction or complete interruption of the transport of gas, fluids, or solids through the conduit. As used herein, "occlusion-initiating material" and "biodegradable cyanoacrylate composition" are used interchangeably and refer to a composition that is capable of occluding a conduit by effecting an occlusion therein. As used herein, occlusion-initiating material means the initial composition (e.g., a biodegradable cyanoacrylate composition) that is placed or inserted into the conduit forms an initial occlusion, and with exposure, the material, through its interaction with the tissue of the conduit, induces or causes the conduit to be closed or occluded so that materials that formerly transited the conduit, such as fluids or solids, no longer can transit the conduit in the area of the occlusion. The occlusion that is formed in the conduit may or may not comprise components of the occlusion-initiating material. For example, an occlusion may comprise only cells or cellular materials of the subject as the occlusion-initiating material has biodegraded. Initially, after provision of the occlusion-initiating material to the conduit, the occlusion at the site may comprise a biodegradable cyanoacrylate composition, and as the biodegradable cyanoacrylate composition degrades, less occlusion-initiating material/cyanoacrylate composition remains at the occlusion site. The meaning of the term can be determined from its use in the sentence. Cyanoacrylate compositions, biodegradable cyanoacrylate compositions, occlusion compositions, cyanoacrylate materials, occlusion-initiating material, occlusion-initiating composition and occlusion materials are terms used START interchangeably herein. In the initial stages, after delivery of the liquid biodegradable cyanoacrylate composition, the occlusion may be primarily formed by the polymerized biodegradable cyanoacrylate composition. Over time, as the polymerized biodegradable cyanoacrylate composition breaks down or is removed from the site of delivery, the occlusion is formed by the cellular reactions and scar tissue or healing outcome by the cells of the site.

Biodegradable cyanoacrylate compositions of the present disclosure may comprise materials that are liquid, semi-solid, gels, solids and combinations thereof. Cyanoacrylate materials may comprise compositions that cure in situ at the desired site of the conduit. Biodegradable cyanoacrylate compositions may further comprise materials that polymerize in situ, wherein the polymerization may be initiated either at the site of the conduit or prior to placement at the site.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, EIZ specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, when a compound is referred to as a monomer or a compound, it is understood that this is not interpreted as one molecule or one compound. For example, two cyanoacrylate monomers refers to two different cyanoacrylate monomers, and not two molecules.

As used herein, the terms "optional" or "optionally" means that the subsequently described event or circumstance can or cannot occur, and that the description includes instances where said event or circumstance occurs and instances where it does not.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "cure" means a change in the physical, chemical, or physical and chemical properties of the cyanoacrylate material following placement or insertion at the desired site in a conduit, and as is generally understood for polymeric materials, "cure" means the composition transforms from a liquid to a solid or semi-solid.

As used herein, the term “subject” can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, a mammalian subject is a human. A patient refers to a subject afflicted with a disease or disorder. The term “patient” includes human and veterinary subjects. In some aspects of the disclosed methods, the subject has been diagnosed with a need for a treatment comprising occluding a conduit prior to the administering of the cyanoacrylate compositions. In some aspects, the subject has been diagnosed with a need for administration of the cyanoacrylate compositions prior to the administering step.

As used herein, the terms “administering” and “administration” refer to any method of providing a disclosed cyanoacrylate composition to a subject.

As used herein, the terms “comprises,” “comprising,” “includes,” “including,” “containing,” “characterized by,” “has,” “having” or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The transitional phrase “consisting of” excludes any element, step, or ingredient not specified in the claim, closing the claim to the inclusion of materials other than those recited except for impurities ordinarily associated therewith. When the phrase “consists of” appears in a clause of the body of a claim, rather than immediately following the preamble, it limits only the element set forth in that clause; other elements are not excluded from the claim as a whole.

The transitional phrase “consisting essentially of” limits the scope of a claim to the specified materials or steps and those that do not materially affect the basic and novel characteristic(s) of the claimed invention. A ‘consisting essentially of’ claim occupies a middle ground between closed claims that are written in a ‘consisting of’ format and fully open claims that are drafted in a ‘comprising’ format. Optional additives as defined herein, at a level that is appropriate for such additives, and minor impurities are not excluded from a composition by the term “consisting essentially of”.

When a composition, a process, a structure, or a portion of a composition, a process, or a structure, is described herein using an open-ended term such as “comprising,” unless otherwise stated the description also includes an embodiment that “consists essentially of” or “consists of” the elements of the composition, the process, the structure, or the portion of the composition, the process, or the structure.

The articles “a” and “an” may be employed in connection with various elements and components of compositions, processes or structures described herein. This is merely for convenience and to give a general sense of the compositions, processes or structures. Such a description includes “one or at least one” of the elements or components. Moreover, as used herein, the singular articles also include a description of a plurality of elements or components, unless it is apparent from a specific context that the plural is excluded.

The term “about” means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is “about” or “approximate” whether or not expressly stated to be such.

The term “or”, as used herein, is inclusive; that is, the phrase “A or B” means “A, B, or both A and B”. More specifically, a condition “A or B” is satisfied by any one of the following: A is true (or present) and B is false (or not present); A is false (or not present) and B is true (or present); or both A and B are true (or present). Exclusive “or” is designated herein by terms such as “either A or B” and “one of A or B”, for example.

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

When materials, methods, or machinery are described herein with the term “known to those of skill in the art”, “conventional” or a synonymous word or phrase, the term signifies that materials, methods, and machinery that are conventional at the time of filing the present application are encompassed by this description. Also encompassed are materials, methods, and machinery that are not presently conventional, but that will have become recognized in the art as suitable for a similar purpose.

Unless stated otherwise, all percentages, parts, ratios, and like amounts, are defined by weight.

All patents, patent applications and references included herein are specifically incorporated by reference in their entireties.

It should be understood, of course, that the foregoing relates only to preferred embodiments of the present disclosure and that numerous modifications or alterations may be made therein without departing from the spirit and the scope of the disclosure as set forth in this disclosure.

The present disclosure is further illustrated by the examples contained herein, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

EXAMPLES

Example 1 Fifty-Two-Week Biodegradable, Cyanoacrylate Composition in Rabbit Oviduct Implantation Study The study involved surgical delivery of a biodegradable cyanoacrylate composition disclosed herein. The biodegradable, cyanoacrylate composition was made, for example, by pre-mixing all the components, 0.42 g methoxypropyl cyanoacrylate (MPCA) and 0.18 g methoxyisopropyl cyanoacrylate (MIPCA) to form a cyanoacrylate component, a stabilizer component, 0.0004 g of $SO_2$ with 0.003 g BHA (butylated hydroxy anisole), a polymerization inhibitor, to form a biodegradable, cyanoacrylate composition. A sufficient amount of the biodegradable, cyanoacrylate composition was made and delivered using a modified PICC-NATE catheter into screened rabbit oviducts to mimic the use in humans and tested in situ polymerization in in vivo oviducts. The effects to the animal over the course of the biodegradable, cyanoacrylate composition's presence in, and degradation out of, the oviducts was assessed. Endpoints of the study were to evaluate the degree and nature of tubal occlusion created by the cyanoacrylate composition, to assess the safety of the cyanoacrylate composition by evaluating local tissue reaction over time during the cyanoacrylate compositions presence and degradation, to characterize the degradation profile of the test article over time, and to provide limited systemic toxicology data.

Thirty-seven New Zealand White female rabbits were successfully dosed with the biodegradable, cyanoacrylate composition. Four were euthanized within days of treatment. Seven sham-treated animals and 27 treated animals underwent pathological analysis. Timepoints were 2 and 4 weeks, 3 months, 6 months and 12 months.

There were no systemic toxicity effects. Other than local cellular reaction, there were no adverse local tissue effects. Complete tubal occlusion was present in 60% of oviducts at 3 and 6 months. The cyanoacrylate material was mostly degraded in 3-6 months, with little residual material at 12 months. The study demonstrated that the cyanoacrylate composition elicited a foreign body response in the oviduct, which resulted in scar tissue to block the oviducts. Administration into the oviducts of rabbits was not observed to produce any signs of systemic toxicity, and produced local treatment-related effects including inflammation, necrosis, and healing responses, primarily limited to the 28 day timepoint. These changes were largely observed to decrease in intensity or were not observed at the 90 day and 180 day timepoints.

Example 2 Test for Cytotoxicity ISO 10993-5

The potential biological reactivity of a mammalian cell culture (mouse fibroblast L929) in response to exposure to the extract of a test article of a polymerized biodegradable, cyanoacrylate composition (test article) as used in Example 1, was determined. The test article was extracted in Minimum Essential Medium (MEM) with 10% fetal bovine serum (referred to as complete MEM) for 24±2 hours at 37±1° C. Negative and positive controls were prepared similarly. The maintenance medium of L929 cells grown in 96-well plates was replaced with the 100% (neat) extracts of the of the test article and control articles in 6 replicates, and the cells were incubated for 24 to 26 hours at 37±1° C. The viability of cells following the exposure to the extracts was measured via their capacity to uptake a vital dye, Neutral Red (NR). This dye was added to the cells to be actively incorporated in viable cells. The number of viable cells correlates to the color intensity determined by photometric measurements after extraction. After exposure time, the cells were washed with PBS (phosphate buffered saline) and sterile Neutral Red medium (50 microgram/mL in MEM without Phenol Red) was added to each test well, and the cells were incubated for 3±0.2 hours in an incubator at 37±1° C. The cells were then washed with PBS, and 150 microliters of ethanol/acetic acid solution was added to each well to extract the NR. Optical density (OD) of each well was then measured.

Negative controls were HDPE (negative control plastic) and positive control was natural rubber. An untreated control, no added plastic or material, was also used.

The viability percentage of the cells exposed to the 100% (neat) test article extract was 17%. The viability percentage of the cells exposed to the negative and positive control articles were grater and lower than 70%, respectively, confirming the validity of the assay. Based on the criteria of the protocol and the ISO 10993-5 guidelines, the test article does not meet the requirements of the test and is considered to have a cytotoxic effect.

The in vitro cytotoxicity study demonstrated that leachate from the polymerized biodegradable, cyanoacrylate composition produced a marked decrease in cell viability. This cytotoxicity was accompanied by observed local implantation site reactivity in the muscle, but not in subcutaneous tissue and extracts of the polymer were not irritating following intradermal injection or application into the vagina of rabbits. The local implantation site reactivity was slight in nature when compared to the reaction produced by the Histoacryl (butyl cyanoacrylate) control implant which is an FDA approved tissue adhesive. Observed local irritation and cytotoxicity is likely attributable to the cyanoacrylates incorporated into the polymer.

Example 3 Pre-Hysterectomy Trial

Implantation of biodegradable, cyanoacrylate compositions in human subjects were performed under all appropriate protocols for human experimentation. Human females who were to undergo a hysterectomy procedure were pretreated by providing a biodegradable, cyanoacrylate composition to at least the cornua of the fallopian tubes using a device disclosed herein. The following biodegradable, cyanoacrylate compositions were used Biodegradable, cyanoacrylate composition 100 wt % MCPA (cyanoacrylate component), BHA 5000 ppm (polymerization inhibitor component), and 2260 $SO_2$ (stabilizer component).

Biodegradable, cyanoacrylate composition 50 wt % MCPA and 50 wt % MIPCA (cyanoacrylate component), BHA 5000 ppm (polymerization inhibitor component), and 2260 $SO_2$ (stabilizer component).

Biodegradable, cyanoacrylate composition 70 wt % MCPA and 30 wt % MIPCA (cyanoacrylate component), BHA 5000 ppm (polymerization inhibitor component), and 2260 $SO_2$ (stabilizer component).

The total abdominal hysterectomy procedure with bilateral salpingectomy was performed at either 28 days or 29 days after administration of the biodegradable cyanoacrylate composition, and the fallopian tubes were examined microscopically and histopathologically. Some subjects showed the presence of polymerized composition, others showed local inflammation and healing response, and complete healing response with occluded fallopian tubes was seen. The responses seen in fallopian tubes to the biodegradable cyanoacrylate composition ranged from some to no material present, slight to marked inflammatory cell patterns, and luminal occlusion due to inflammatory healing reactions. When the material was present, inflammatory reactive cells were also present. One patient's fallopian tube showed a 70-90% stenosis of a 2 mm length followed by 2 mm length that was 100% occluded in the interstitial segment transitioning into the isthmus segment having a 2 mm length that was 50-80% stenosed and progressing to an 18 mm length of complete luminal occlusion, 100%. Full luminal occlusion was shown in three fallopian tubes, and two others showed 50-90% occlusion. Inflammatory response generally correlated with presence of the polymerized composition.

What is claimed is:

1. A biodegradable cyanoacrylate composition, consisting essentially of, a) a cyanoacrylate component consisting of methoxyisopropyl cyanoacrylate and methoxypropyl cyanoacrylate, wherein the cyanoacrylate component is 99 wt % or greater of the total weight of the biodegradable cyanoacrylate composition;

b) a stabilizer component of sulfur dioxide in a range from 600 ppm to 1500 ppm; and c) a polymerization inhibitor component of butylated hydroxy anisole (BHA) in a range from 4000 to 7000 ppm, wherein the viscosity of the composition is from about 10 cP to about 30 cP;

with a cure or setting time between 10 seconds and 30 seconds; and wherein the composition fails to pass a Neutral Red cytotoxicity test (as measured by ISO 10993-5:2009) and passes genotoxicity testing (as measured by ISO 10993-3:2003).

2. The biodegradable cyanoacrylate composition of claim 1, further comprising a plasticizing agent, biocompatible agent, thickening agent, medicament, crosslinking agent, dye or pigment, preservative, antimicrobial agent, or polymerization initiator or accelerator.

3. The biodegradable cyanoacrylate composition of claim 1, wherein the composition is sterile.

4. A biodegradable cyanoacrylate composition, comprising, a. a cyanoacrylate component consisting of methoxyisopropyl cyanoacrylate and methoxypropyl cyanoacrylate, wherein the cyanoacrylate component is 99 wt % or greater of the total weight of the biodegradable cyanoacrylate composition;

b. a stabilizer component of sulfur dioxide in a range from 600 ppm to 1500 ppm; and c. a polymerization inhibitor component of butylated hydroxy anisole (BHA) in a range from 4000 to 7000 ppm.

5. The biodegradable cyanoacrylate composition of claim 4, further comprising a plasticizing agent, biocompatible agent, thickening agent, medicament, crosslinking agent, dye or pigment, preservative, antimicrobial agent, or polymerization initiator or accelerator.

6. The biodegradable cyanoacrylate composition of claim 4, wherein the composition is sterile.

7. The biodegradable cyanoacrylate composition of claim 5, wherein the composition is sterile.

* * * * *